United States Patent
Morris et al.

(10) Patent No.: US 12,109,279 B2
(45) Date of Patent: Oct. 8, 2024

(54) SELF-BUBBLING PEEL-AWAY CLEANSING MASK

(71) Applicant: L'OREAL, Paris (FR)

(72) Inventors: Stephanie Anne Ventura Morris, Montclair, NJ (US); Ryuji Hara, Westfield, NJ (US)

(73) Assignee: L'OREAL, Paris (FR)

( * ) Notice: Subject to any disclaimer, the term of this patent is extended or adjusted under 35 U.S.C. 154(b) by 275 days.

(21) Appl. No.: 17/002,356

(22) Filed: Aug. 25, 2020

(65) Prior Publication Data

US 2022/0062118 A1    Mar. 3, 2022

(51) Int. Cl.
*A61K 8/02* (2006.01)
*A61K 8/60* (2006.01)
*A61K 8/891* (2006.01)
*A61Q 19/10* (2006.01)

(52) U.S. Cl.
CPC .............. *A61K 8/0212* (2013.01); *A61K 8/60* (2013.01); *A61K 8/891* (2013.01); *A61Q 19/10* (2013.01)

(58) Field of Classification Search
None
See application file for complete search history.

(56) References Cited

U.S. PATENT DOCUMENTS

| | | |
|---|---|---|
| 5,741,509 A | 4/1998 | Kushner |
| 6,172,019 B1 | 1/2001 | Dehan et al. |
| 8,263,114 B2 | 9/2012 | Berlat |
| 2002/0122772 A1 | 9/2002 | Lukenbach et al. |
| 2006/0018853 A1 | 1/2006 | Watanabe |
| 2008/0292560 A1* | 11/2008 | Tamarkin ............... A61K 8/731 424/45 |
| 2019/0269604 A1 | 9/2019 | Kim et al. |
| 2021/0030652 A1 | 2/2021 | Stebbins et al. |

FOREIGN PATENT DOCUMENTS

| | | |
|---|---|---|
| CN | 103356425 | 10/2013 |
| JP | 55127311 | 10/1980 |

OTHER PUBLICATIONS

GNPD MINTEL, "Charcoal Detox Peel-Off Mask", No B.S. Life, Record ID No. 6640051, accessed on Aug. 5, 2021.
GNPD MINTEL, "CDouble Bubble Purifying Mask", Clinique, Record ID No. 4928537 accessed on Aug. 5, 2021.

* cited by examiner

*Primary Examiner* — Nannette Holloman
(74) *Attorney, Agent, or Firm* — Laetitia Leproust; Robert Klemz

(57) ABSTRACT

Cleansing compositions are provided. The mask cleansing composition includes a) A polyvinyl alcohol; b) At least one sugar alcohol; c) At least one surfactant; d) At least one or more hydrophobically-modified polymers; e) At least one silicone oil; and wherein the composition provides the self-bubbling action. The cleansing composition is free of perfluoro compound.

14 Claims, No Drawings

SELF-BUBBLING PEEL-AWAY CLEANSING MASK

FIELD OF THE DISCLOSURE

The present disclosure relates to a self-bubbling peel-away cleansing mask composition.

BACKGROUND

One goal of the cosmetic field is to deliver highly effective products with skin benefits such as hydration, moisturizing, whitening, cleansing, and so on to the consumers.

Among all the compositions for caring for keratin materials, in particular the skin, masks are known to have high penetration efficacy on the keratin materials. But they do use a certain amount of water in order to remove them.

Therefore, it is an object of the present disclosure to create a cleansing mask product that provides not only deep cleansing properties, but also contributes to limit the water consumption.

In view of the remarks above, it would be beneficial to provide a mask composition for cleansing the skin that uses less water than a traditional cleansing mask. Here we present such a composition that forms a film on the skin that can be removed by peeling it away from the skin surface in one piece without using water and also has a unique sensory aspect of self-bubbling. Furthermore, the self-bubbling action is achieved without the use of perfluorinated compounds which are known to incur several environmental and health concerns. It will also be unique in its ability to have a good deposition of skin active ingredients.

SUMMARY OF THE DISCLOSURE

The instant disclosure relates to cleansing masks composition comprising:
  a) From about 8 to about 20 wt. % of a polyvinyl alcohol;
  b) From about 0.2 to about 10 wt. % of at least one sugar alcohol;
  c) From about 0.1 to about 50 wt. % of at least one surfactant;
  d) From about 0.2 to about 2 wt. % of at least one or more hydrophobically-modified polymers;
  e) At least one silicone oil; and
    wherein the composition provides the self-bubbling action; and
    wherein the weight percentages are based on the total weight of the cleansing composition.

The cleansing mask compositions of the instant case are free of perfluoro compound. Despite the lack of the perfluoro compound, the cleansing mask compositions of the instant case can start self-bubbling immediately after application of the composition onto the skin.

In one or more embodiments, the cleansing composition peels away in one piece from the skin.

In one or more embodiments, the cleansing composition dries down into a film, said film can be peeled away in one piece in less than 10 minutes.

In some embodiments, the polyvinyl alcohol is present from about 10 to about 16 wt. % of the total weight of the cleansing composition.

In one or more embodiments, the at least one sugar alcohols is selected from the group chosen from isomalt, mannitol, galactilol, fucitol, iditol, volemitol, lactitol, maltotriiol, maltotetraitol, polyglycitol, sorbitol, xylitol, lactitol, maltitol, inositol, erythritol, hydrogenated starch hydrolysates, and mixtures thereof.

In one or more embodiments, the at least one surfactant is selected from the group consisting of anionic surfactants, non-ionic surfactants, zwitterionic surfactants and combinations thereof. In some embodiments, the at least one surfactant is selected from disodium laureth sulfosuccinate, sodium lauryl sulfoacetate, PEG-7 Glyceryl Cocoate, cocobetaine and combinations thereof.

In one or more embodiments, the one or more hydrophobically-modified polymers is selected from cetyl hydroxyethylcellulose, acrylates/beheneth-25 methacrylate copolymer, acrylates/c10-30 alkyl acrylate crosspolymer, acrylates/vinyl neodecanoate crosspolymer, ammonium acryloyldimethyltaurate/steareth-25 methacrylate crosspolymer, ammonium polyacryloyldimethyl taurate, glyceryl polyacrylate, ethyl hydroxyethylcellulose, methyl hydroxyethylcellulose, hydroxypropyl guar, hydroxypropyl starch phosphate, peg-240/hdi copolymer bis-decyltetradeceth-20 ether, polyacrylate crosspolymer-6, steareth-100/peg-136/hdi copolymer, and combination thereof.

In one or more embodiments, the at least one silicone oil is a cyclic or linear silicone molecule having a viscosity of less than 8 cst. In some embodiments, the at least one silicone oil is selected from disiloxane, hexamethyldisiloxane, divinyltetramethyldisiloxane, octamethyldisiloxane, decamethyltetrasiloxane, hexadecamethylheptasiloxane, dodecamethylpentasiloxane, hexamethylcyclotrisiloxane, tetradecamethylhexasiloxane, octamethylcyclotetrasiloxane, decamethylcyclopentasiloxane, dodecamethylcyclohexasiloxane, polydimethylsiloxane, ethyl trisiloxane, and combinations thereof. In some embodiments, the at least one silicone oil is present from about 0.1 to 5 wt. % of the total weight of the cleansing composition.

In one or more embodiments, the self-bubbling action is provided by the presence of the at least one silicone oil.

In one or more embodiments, the composition is free of perfluoro compounds.

In some embodiments, cleansing mask compositions may contain:
  a) From about 6 to about 20 wt. % of polyvinyl alcohol;
  b) From about 0.2 to about 10 wt. % of at least one sugar alcohol comprising Hydrogenated Starch Hydrosylate;
  c) From about 0.1 to about 50 wt. % of at least one surfactant selected from disodium laureth sulfosuccinate, sodium lauryl sulfoacetate, PEG-7 Glyceryl Cocoate, coco-betaine and combination thereof;
  d) From about 0.2 to about 2 wt. % of at least one hydrophobically-modified polymer comprising cetyl hydroxyethylcellulose;
  e) From about 0.1 to about 5 wt. % of disiloxane; and
    wherein the composition provides the self-bubbling action;
    wherein the composition is free of perfluoro compounds; and
    wherein the weight percentages are based on the total weight of the cleansing composition.

In one or more embodiments, the self-bubbling composition self-bubble within 10 seconds after application of the cleansing composition onto the skin.

The bubbles may be able to form quickly for example within less than about 10 seconds, within less than about 9 seconds, within less than about 8 seconds, within less than about 7 seconds, within less than about 6 seconds, within less than about 5 seconds, within less than about 4 seconds, within less than about 3 seconds, within less than about 2 seconds, within less than about 1 seconds after application of the cleansing composition onto the skin.

In some embodiments, cleansing compositions may comprise:
a) From about 6 to about 20 wt. % of polyvinyl alcohol;
b) From about 0.2 to about 10 wt. % of at least one sugar alcohol comprising Hydrogenated Starch Hydrosylate;
c) From about 0.1 to about 50 wt. % of at least one surfactant selected from disodium laureth sulfosuccinate, sodium lauryl sulfoacetate, PEG-7 Glyceryl Cocoate, coco-betaine and combination thereof;
d) From about 0.2 to about 2 wt. % of at least one hydrophobically-modified polymer comprising cetyl hydroxyethylcellulose;
e) From about 0.1 to about 5 wt. % of disiloxane; and
wherein the composition provides the self-bubbling action;
wherein the composition is free of perfluoro compounds; and
wherein the weight percentages are based on the total weight of the cleansing composition.

The cleansing compositions are useful for treating the skin, in particular the skin of the face. The compositions can be used as a facial wash, and/or makeup remover, as the products are particularly effective at cleansing the skin.

Some aspects of the instant disclosure can include a method for cleansing the skin comprising applying the composition to the skin and removing the composition from the skin by peeling away the composition in one piece.

Some aspects of the instant disclosure can include a method for cleansing the skin comprising applying the composition to the skin and removing at least a portion of the composition from the skin.

Another aspects of the instant disclosure can include a method for cleansing the face comprising applying the composition to the face and cleansing the face.

The methods generally include applying the cleansing compositions to the skin.

The cleansing compositions of the instant disclosure provide unexpected self-bubbling once in contact with the skin as well as an unexpected formation of a film than can be removed from the skin in one gesture and peels off in one piece thanks to the compositions described in the instant disclosure.

Without being bound by theory or mechanism, it is suggested that the self-bubbling starting at the contact of the skin is due to the rapid evaporation of the volatile silicone oil when the bulk formula is spread thin.

It is to be understood that both the foregoing general description and the following detailed description are exemplary and explanatory only, and are not restrictive of the invention.

DETAILED DESCRIPTION OF THE DISCLOSURE

The instant disclosure relates to compositions for cleansing the skin.

The cleansing mask compositions of the instant disclosure, in their broadest sense, typically include the following:
a) From about 8 to about 20 wt. % of a polyvinyl alcohol;
b) From about 0.2 to about 10 wt. % of at least one sugar alcohol;
c) From about 0.1 to about 50 wt. % of at least one surfactant;
d) From about 0.2 to about 2 wt. % of at least one or more hydrophobically-modified polymers;
e) At least one silicone oil; and
wherein the composition provides the self-bubbling action; and
wherein the weight percentages are based on the total weight of the cleansing composition.

The cleansing composition disclosed herein starts self-bubbling immediately after application of the composition onto the skin. In some embodiments, the self-bubbling composition is self-bubbling within 10 seconds after application of the cleansing composition onto the skin. The self-bubbling, then, last at least about 3 minutes, at least about 3.5 minutes or more. Once, the composition is dried down into a film in less than about 10 minutes, the cleansing mask can be peeled away in one piece from the skin.

As used herein, the term "peel-away" means that the product peels away from the skin. The combination of ingredients creates a peelable film or a peel-off mask.

As used herein, the term "peel-off mask" and "peel away" are used interchangeably throughout the instant disclosure.

As used herein, the term "self-bubbling" means that it is a composition that exhibits bubbles only when applied in a thin layer to the skin without the additional of any other exterior stimuli.

As used herein, the term "critical micelle concentration" means the chemical concentration at which aggregates start to self-assemble.

Polyvinyl Alcohol

As used herein, the term "polyvinyl alcohol" is understood within the instant disclosure to mean a polymer comprising —CH2CH(OH)— groups with 1,3-diol linkages and/or 1,2-diol linkages.

The polymer providing the peelable film formation action needs to have high elongation at break, such that the film formed is flexible and not brittle. It also should have medium adhesion, so that it binds the gel into a film but can still be easily lifted from the skin.

The polyvinyl alcohols are generally produced by hydrolysis of polyvinyl acetate via transesterification. The degree of hydrolysis of commercial products is variable, often around 87%, but there are also products with a degree of hydrolysis of 100%. Copolymers with monomers other than vinyl acetate also exist, such as ethylene/vinyl alcohol copolymers.

The polyvinyl alcohol polymers as thickening polymers are preferably chosen from homopolymers or copolymers with vinyl acetate, the latter corresponding in particular to a partial hydrolysis of polyvinyl acetate.

Use may be made, for example, of the products from the Selvol range sold by SEKISUI SPECIALTY CHEMICALS under the names SELVOL™ ULTRALUX FF, Selvol™125, Selvol™ 103, Selvol™ 325, Selvol™ 523, Selvol™ 540, Selvol™ 205, Selvol™ 203, Selvol™ Polyvinyl Alcohols 805, Selvol™ Polyvinyl Alcohols 823, Selvol™ Polyvinyl Alcohols 840, Selvol™ Polyvinyl Alcohol 203S, 205S, 523S and 540S.

The composition according to the instant disclosure advantageously comprises from 8 to 20%, preferably from 10 to 15% by weight of one or more polyvinyl alcohols relative to the total weight of the composition.

The one or more polyvinyl alcohols of the instant disclosure may be employed in an amount of from about 8, 8.2, 8.4, 8.6, 8.8, 9, 9.2, 9.4, 9.6, 9.8, 10, 10.2, 10.4, 10.6, 10.8, 11, 11.2, 11.4, 11.6, 11.8, 12, 12.2, 12.4, 12.6, 12.8, 13, 13.2, 13.4, 13.6, 13.8, 14, 14.2, 14.4, 14.6, 14.8, 15, 15.2, 16.4, 15.6, 15.8, 16 to about 16, 16.2, 16.4, 16.6, 16.8, 17, 17.2, 17.4, 17.6, 17.8, 18, 18.2, 18.4, 18.6, 18.8, 19, 19.2, 19.4, 19.6, 19.8 or 20 wt. % of the total weight of the cleansing mask compositions.

Sugar Alcohols

A sugar alcohol is a polyol produced by hydrogenation of sugars.

Non-limiting examples of sugar alcohols include isomalt, mannitol, galactilol, fucitol, iditol, volemitol, lactilol, maltotriiol, maltotetraitol, polyglycitol, sorbitol, xylitol, lactitol, maltitol, inositol, erythritol, and mixtures thereof. In some cases, the one or more sugar alcohols includes hydrogenated starch hydrolysates.

The total amount of the one or more sugar alcohols can vary but is typically about 0.2 to about 10 wt. %, of the total weight of the cleansing mask compositions.

The total amount of the one or more sugar alcohols may be about 0.2, 0.3, 0.4, 0.6, 0.8, 1, 1.2, 1.4, 1.6, 1.8, 2, 2.2, 2.4, 2.6, 2.8, 3, 3.2, 3.4, 3.6, 3.8, 4, 4.2, 4.4, 4.6, 4.8 to about 4.8, 5, 5.1, 5.2, 5.3, 5.4, 5.5, 5.6, 5.7, 5.8, 5.9, 6, 6.2, 6.4, 6.6, 6.8, 7, 7.2, 7.4, 7.6, 7.8, 8, 8.2, 8.4, 8.6, 8.8, 9, 9.2, 9.4, 9.6, 9.8, or 10 wt. % of the total weight of the cleansing mask compositions.

Surfactants

In some embodiments, the one or more surfactants may be selected from the following classes of surfactants: Carboxylates, Alkyl ether carboxylates, Alkyl sarcosinates, Sulfates, Alkyl ether sulfates, Alkyl sulfates, Alkyl taurates, Sulfonates, Alkyl sulfonates, Alkylbenzene sulfonates, Sulfosuccinate esters, Dialkyl sulfosuccinates, Alkyl sulfosuccinates, Paraffin sulfonates, α-olefin sulfonates, Isethionates, Phosphates, Alkyl phosphates, Alkyl ether phosphates, Polyethers, Fatty acid ethoxylates, fatty alcohol ethoxylates, Alkylphenol ethoxylates, Fatty amide ethoxylates, Fatty amine ethoxylates, Ethoxylated triglycerides, Fatty acid methyl ester ethoxylates, Poloxamers, Sucrose esters, Sorbitan esters, Sorbitan alkyl esters, Alkyl glucosides, Alkyl polyglucosides, Sorbitan alkanoate, Ethoxylated sorbitan alkanoates, Acetylenic glycols, N-alkyl derivatives of simple amino acids, Glycinates, Betaines, Amido betaines, Alkyl betaines, Pyrophosphobetaines, Aminopropionates, Alkyl amphopropionates, Alkyl amphodipropionates, Glutamates, Cocoates, Imidazolines, N-oxides of tertiary amines, Alkyl amphoacetate, Alkyl amphodiacetate, Hydroxysultaines and mixtures thereof.

Surfactants in the composition include a single surfactant or a mixture of surfactants (often surfactant powders or in other easily used forms (liquid)). In one embodiment, the composition includes one or more surfactants that includes anionic, zwitterionic, non-ionic surfactants and combinations thereof.

Zwitterionic Surfactant

Non-limiting zwitterionic surfactants include, for example, coco-betaine, lauryl betaine, oxyethylenated (10 EO) lauryl betaine, oxyethylenated (10 EO) stearyl betaine, cocamidopropyl betaine, lauramidopropyl betaine and mixtures thereof.

The surfactant in the composition according to the instant disclosure may be one zwitterionic surfactant chosen from betaines, (C8-C20)alkyl betaines, (C8-C20)alkylamido (C1-C6)alkylbetaines, and mixtures thereof. Two or more zwitterionic surfactants may be used in combination. Thus, a single type of zwitterionic surfactant or a combination of different types of zwitterionic surfactants may be used.

Examples of zwitterionic surfactants include surfactants selected from these classes of surfactants: N-alkyl derivatives of simple amino acids, Glycinates, Betaines, Amido betaines, Alkyl betaines, Pyrophosphobetaines, Aminopropionates, Alkyl amphopropionates, Alkyl amphodipropionates, Glutamates, Cocoates, Imidazolines, N-oxides of tertiary amines, Alkyl amphoacetate, Alkyl amphodiacetate, Hydroxysultaines. In selected embodiments, the preferred surfactants are those having alkyl and alkylarye chains in the C10 to C18 range.

Mention may in particular be made, as betaines, of (C8-C20)alkyl betaines, such as, for example, coco betaine, such as the product sold under the name Dehyton AB-30® by the company Cognis, lauryl betaine, such as the product sold under the name Genagen KB® by the company Clariant, oxyethylenated (10 EO) lauryl betaine, such as the product sold under the name Lauryl Ether (10 EO) Betaine® by the company Shin Nihon Rica, or oxyethylenated (10 EO) stearyl betaine, such as the product sold under the name Stearyl Ether (10 EO) Betaine® by the company Shin Nihon Rica, DEHYTON AB 30 by the company BASF.

Mention may be made, among (C8-C20)alkylamido (C1-C6)alkylbetaines and derivatives thereof, for example, of cocamidopropyl betaine, sold under the name Lebon 2000 HG® by the company Sanyo or sold under the name Empigen BBQ by the company Albright & Wilson, or lauramidopropyl betaine, sold under the name Rewoteric AMB12P® by the company Witco.

Preferably, the zwitterionic surfactant is chosen from (C8-C20)alkyl betaines, (C8-C20)alkylamido (C1-C6)alkylbetaines, and mixtures thereof, and preferably among coco betaine, lauryl betaine, oxyethylenated (10 EO) lauryl betaine, oxyethylenated (10 EO) stearyl betaine, cocamidopropyl betaine and mixtures thereof, and more preferably is selected from lauryl betaine, coco betaine and mixtures thereof and still more preferably is coco betaine.

Anionic Surfactants

In some embodiments, one surfactant can be, for example, a compound selected from the group consisting of sodium lauroyl glutamate, sodium lauryl sulfate, disodium lauryl sulfosuccinate, diethylhexyl sodium sulfosuccinate, sodium cocoyl glycinate, potassium cocoyl glycinate, and the mixtures thereof.

In some embodiments, one of the surfactants is disodium lauryl sulfosuccinate.

Examples of anionic surfactants include surfactants selected from these classes of surfactants: Carboxylates, Alkyl ether carboxylates, Alkyl sarcosinates, Sulfates, Alkyl ether sulfates, Alkyl sulfates, Alkyl taurates, Sulfonates, Alkyl sulfonates, Alkylbenzene sulfonates, Sulfosuccinate esters, Dialkyl sulfosuccinates, Alkyl sulfosuccinates, Paraffin sulfonates, α-olefin sulfonates, Isethionates, Phosphates, Alkyl phosphates, Alkyl ether phosphates Alternative surfactants may include or be combined with cleansing surfactants or cleansing agents suitable for use in skin cleansers or on skin cleansing fibrous pads.

Non Ionic Surfactants

In some embodiments, one of the surfactant is PEG-7 Glyceryl Cocoate.

Useful non ionic surfactants include, but are not limited to, the following surfactant classes: Polyethers, Fatty acid ethoxylates, Fatty alcohol ethoxylates, Alkylphenol ethoxylates, Fatty amide ethoxylates, Fatty amine ethoxylates, Ethoxylated triglycerides, Fatty acid methyl ester ethoxylates, Poloxamers, Sucrose esters, Sorbitan esters, Sorbitan alkyl esters, Alkyl glucosides, Alkyl polyglucosides, Sorbitan alkanoate, Ethoxylated sorbitan alkanoates, Acetylenic glycols, and a mixture thereof.

In alternative embodiments, the surfactant may include suitable nonionic surfactants including alkyl polyglucoside having alkyl groups from C10 to C16.

Other Surfactants

According to the instant disclosure, these surfactants can be chosen from salts, for example, alkali metal salts such as sodium salts, potassium salts, ammonium salts, calcium salts, amine salts, amino alcohol salts and alkaline-earth metal salts.

Examples of alkaline-earth metal salts include magnesium salts of the following types of compounds: acyl isethionates, acyl glycinates, acyl taurates, acyl amino acids, acyl sarcosinates, sulfosuccinates, sulfonates, and sulfoacetates, the alkyl and acyl groups of all these compounds comprising from 6 to 24 carbon atoms (saturated or unsaturated, linear or branched).

Non-limiting examples of acyl amino acids useful in the compositions of the invention include those having the following formula (I):

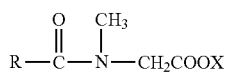

(I)

in which
R is a linear or branched, saturated or unsaturated C8-C16 and more preferentially C12-C18 alkyl chain;
X is an organic cation, for instance an alkanolamine such as triethanolamine, or a mineral cation, for instance an alkali metal such as sodium or potassium, or alternatively ammonia.
Among the preferred radicals R, mention may be made of stearyl, myristyl, oleyl, lauryl and cocoyl.
Among the N-acyl sarcosinates that may be used according to the invention, mention may be made of sodium lauroyl sarcosinate (INCI name: Sodium lauroyl sarcosinate) sold under the name Sarkosyl NL 97® by the company Ciba or sold under the name Oramix L 30® by the company SEPPIC, or sold under the name Amin LS30L by the company Guangzhou Tinci Materials; sodium myristoyl sarcosinate (INCI name: Sodium myristoyl sarcosinate) sold under the name Nikkol Sarcosinate MN® by the company Nikkol, sodium palmitoyl sarcosinate (INCI name: Sodium palmitoyl sarcosinate) sold under the name Nikkol Sarcosinate PN® by the company Nikkol.

Use will be made more particularly of sodium N-lauroyl sarcosinate (INCI name: Sodium lauroyl sarcosinate).

Non-limiting examples of taurates useful in the compositions of the invention include those having the following formula (II):

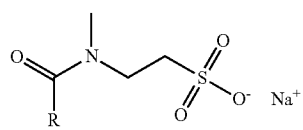

(II)

wherein R is selected from H or an alkyl chain that has 1-24 carbon atoms, said chain being saturated or unsaturated, linear or branched.

A particular taurate that can be used in the current compositions is sodium methyl cocoyl taurate.

Non-limiting examples of isethionates useful in the compositions of the invention include those having the formulas (III) or (IV) below:

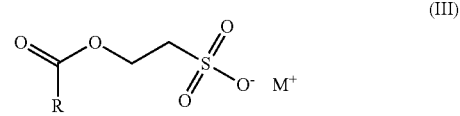

(III)

and

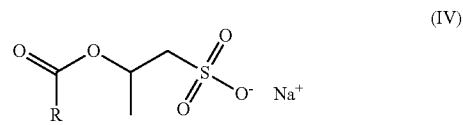

(IV)

wherein R is selected from H or an alkyl chain that has 1-24 carbon atoms, said chain being saturated or unsaturated, linear or branched.

Particular isethionates that can be used in the current compositions include, for example, sodium cocoyl isethionate, sodium lauroyl methyl isethionate, and mixtures thereof.

Non-limiting examples of sulfosuccinates useful in the compositions of the invention include those having the following formula (V):

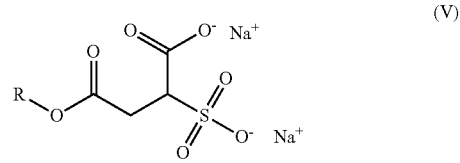

(V)

wherein R is selected from H or an alkyl chain that has 1-24 carbon atoms, said chain being saturated or unsaturated, linear or branched.

A particular sulfosuccinate that can be used in the current compositions is disodium laureth sulfosuccinate.

Non-limiting examples of sulfonates useful in the compositions of the invention include those having the following formula (VI):

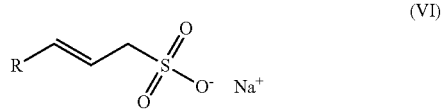

(VI)

wherein R is selected from H or an alkyl chain that has 1-24 carbon atoms, said chain being saturated or unsaturated, linear or branched.

A particular sulfonate that can be used in the current compositions is sodium C14-16 olefin sulfonate.

Non-limiting examples of sulfoacetates useful in the compositions of the invention include those having the following formula (VII):

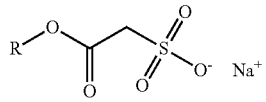
(VII)

wherein R is as defined above for the sulfonates.

A particular sulfoacetate that can be used in the current compositions is sodium lauryl sulfoacetate.

According to one embodiment, the anionic surfactant that is most preferred in the instant disclosure is acyl amino acids useful in the compositions of the invention include those having the following formula (I) as described above, more preferably N-acyl sarcosinates, even more preferably sodium lauroyl sarcosinate (INCI name: Sodium lauroyl sarcosinate).

The total amount of one or more surfactants may be present from about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9 2.0, 2.1, 2.2, 2.5, 3, 3.4, 3.6, 3.8, 4.0, 4.2, 4.4, 4.6, 4.8, 5.0, 5.2, 5.4, 5.6, 5.8, 6.0, 6.2, 6.4, 6.6, 6.8, 7.0, 7.2, 7.4, 7.6, 7.8, 8.0, 8.2, 8.4, 8.6, 8.8, 9.0, 9.2, 9.4, 9.6, 9.8, 10 to about 10, 10.2, 10.4, 10.6, 10.8, 11, 11.2, 11.4, 11.6, 11.8, 12.0, 12.2, 12.4, 12.6, 12.8, 13.0, 13.2, 13.4, 13.6, 13.8, 14.0, 14.2, 14.4, 14.6, 14.8, 15.0, 15.2, 15.4, 15.6, 15.8, 16.0, 16.2, 16.4, 16.6, 16.8, 17.0, 17.2, 17.4, 17.6, 17.8, 18.0, 18.2, 18.4, 18.6, 18.8, 19.0, 19.2, 19.4, 19.6, 19.8, 20.0, 20.2, 20.4, 20.6, 20.8, 21.0, 21.2, 21.4, 21.6, 21.8, 22.0, 22.2, 22.4, 22.6, 22.8, 23.0, 23.2, 23.4, 23.6, 23.8, 24.0, 24.2, 24.4, 24.6, 24.8, or 25 wt. % wt. of the total weight of the cleansing mask compositions.

Emulsifiers

Hydrophobically-Modified Polymers

Hydrophobically-modified polymers are water-soluble polymers onto which relatively low molecular weight hydrophobic side chains have been grafted.

In some embodiments, the one or more hydrophobically-modified polymer emulsifiers is selected from acrylates/C10-30 alkyl acrylate crosspolymer, acrylates/C12-22 alkylmethacrylate copolymer, acrylates/steareth-20 methacrylate copolymer, acrylates/steareth (or ceteth)-20 itaconate copolymer, acrylates/steareth-50 acrylate copolymer, steareth-10 allyl ether/acrylate copolymer, acrylates/beheneth-25 methacrylate copolymer, acrylates/vinyl acetate crosspolymer, glyceryl polymethacrylate, ammonium acryloyldimethyltaurate/beheneth-25 methacrylate copolymer, and a mixture thereof.

Non-limiting examples of hydrophobically modified poly(meth)acrylates include acrylates/C10-30 alkyl acrylate crosspolymer, acrylates/C12-22 alkylmethacrylate copolymer, acrylates/steareth-20 methacrylate copolymer, acrylates/steareth (or ceteth)-20 itaconate copolymer, acrylates/steareth-50 acrylate copolymer, steareth-10 allyl ether/acrylate copolymer, acrylates/beheneth-25 methacrylate copolymer, acrylates/vinyl acetate crosspolymer, glyceryl polymethacrylate, ammonium acryloyldimethyltaurate/beheneth-25 methacrylate copolymer, and a mixture thereof. In some instances, acrylates/beheneth-25 methacrylate copolymer is particularly preferred. Acrylates/beheneth-25 methacrylate copolymer is commercially available from Lubrizol under the tradename of NOVETHIX-L10 Polymer or from Rohm and Haas (Dow Chemical) under the tradename of ACULYN 28.

In certain exemplary and non-limiting embodiments, the copolymers are chosen from the copolymers resulting from the polymerization of:

at least one monomer of formula (II):

$CH_2=CH(R_1)COOH$ (II)

wherein R1 is chosen from H or CH3 or C2H5, providing acrylic acid, methacrylic acid, or ethacrylic acid monomers, and at least one monomer of (C10 C30)alkyl ester of unsaturated carboxylic acid type corresponding to the monomer of formula (III):

$CH_2=CH(R_2)COOR_3$ (III)

wherein R2 is chosen from H or CH3 or C2H5, providing acrylate, methacrylate or ethacrylate units, R3 denoting a C10 C30 alkyl radical, such as a C12 C22 alkyl radical.

Non-limiting examples of (C10 C30)alkyl esters of unsaturated carboxylic acids are for example chosen from lauryl acrylate, stearyl acrylate, decyl acrylate, isodecyl acrylate, dodecyl acrylate and the corresponding methacrylates, such as lauryl methacrylate, stearyl methacrylate, decyl methacrylate, isodecyl methacrylate and dodecyl methacrylate, and mixtures thereof.

Additionally, crosslinked polymers may be chosen according to further exemplary embodiments. For example, such polymers may be chosen from polymers resulting from the polymerization of a mixture of monomers comprising:
acrylic acid,
an ester of formula (III) described above, in which R2 is chosen from H or CH3, R3 denoting an alkyl radical having from 12 to 22 carbon atoms, and
a crosslinking agent, which is a well-known copolymerizable polyethylenic unsaturated monomer, such as diallyl phthalate, allyl (meth)acrylate, divinylbenzene, (poly)ethylene glycol dimethacrylate and methylenebisacrylamide.

By way of example, crosslinked polymers comprising about 60% to about 95% by weight of acrylic acid (hydrophilic unit), about 4% to about 40% by weight of C10 C30 alkyl acrylate (hydrophobic unit), and about 0% to about 6% by weight of crosslinking polymerizable monomer. In yet further embodiments, the crosslinked polymers may comprise about 96% to about 98% by weight of acrylic acid (hydrophilic unit), about 1% to about 4% by weight of C10 C30 alkyl acrylate (hydrophobic unit), and about 0.1% to 0.6% by weight of crosslinking polymerizable monomer, such as those described above.

Such copolymers may be selected, for example, from acrylate/C10 C30 alkyl acrylate copolymers (INCI name: Acrylates/C10-30 Alkyl Acrylate Crosspolymer), such as the products sold by Lubrizol under the trade names PEMULEN™ TR1, PEMULEN™ TR2, CARBOPOL® 1382 and CARBOPOL® EDT 2020.

In further embodiments, the at least one hydrophobically modified polymer may be chosen from nonionic homopolymers or copolymers containing ethylenically unsaturated monomers of the ester and/or amide type. Examples of such agents include the products sold under the names CYANAMER P250 by the company CYTEC (polyacrylamide), methyl methacrylate/ethylene glycol dimethacrylate copolymers (such as PMMA MBX-8C by the company US COSMETICS), butyl methacrylate/methyl methacrylate copolymers (such as ACRYLOID B66 by the company RHOM HMS), and polymethyl methacrylates (BPA 500 by the company KOBO) may be chosen.

We can mention the associative copolymer of the product sold under the commercial name: NOVETHIX L-10 POLYMER® (INCI name: ACRYLATES/BEHENETH-25 METHACRYLATE COPOLYMER) sold by LUBRIZOL, the product sold under the commercial name: Aculyn® 22 (INCI name: ACRYLATES/STEARETH-20 METHACRYLATE COPOLYMER) sold by DOW CHEMICAL, the product sold under the commercial name: Aculyn® 88 (INCI name: ACRYLATES/STEARETH-20 METHACRYLATE CROSSPOLYMER) sold by DOW CHEMICAL, the product sold under the commercial name: STRUCTURE® 2001 (INCI name: ACRYLATES/STEARETH-20 ITACONATE COPOLYMER) sold by AKZO NOBEL, and the product sold under the commercial name: STRUCTURE® 3001 (INCI name: ACRYLATES/CETETH-20 ITACONATE COPOLYMER) sold by AKZO NOBEL.

The one or more hydrophobically-modified polymer thickeners of the instant disclosure may be employed in an amount of from about 0.2, 0.3, 0.4, 0.5 0.6, 0.7, 0.8 to about 0.8, 0.9, 1, 1.1, 1.2, 1.3, 1.4, 1.5, 1.6, 1.7 1.8, 1.9, or 2 wt. of the total weight of the mask cleansing composition.

Gums and Polysaccharides

A wide variety of gums and polysaccharides can be useful herein as gelling agents. "Polysaccharides" refer to gelling agents that contain a backbone of repeating sugar (i.e., carbohydrate) units. Non-limiting examples of polysaccharide gelling agents include those selected from the group consisting of cellulose, carboxymethyl hydroxyethylcellulose, cellulose acetate propionate carboxylate, hydroxyethylcellulose, hydroxyethyl ethylcellulose, hydroxypropylcellulose, hydroxypropyl methylcellulose, methyl hydroxyethylcellulose, microcrystalline cellulose, sodium cellulose sulfate, and mixtures thereof. Also useful herein are the alkyl-substituted celluloses. Preferred among the alkyl hydroxyalkyl cellulose ethers is the material given the CTFA designation cetyl hydroxyethylcellulose, which is the ether of cetyl alcohol and hydroxyethylcellulose. This material is sold under the tradename Polysurf™ 67 CS from Ashland. Further polysaccharides include starch derivatives (for example, starch oxide, dialdehyde starch, dextrin, British gum, acetyl starch, starch phosphate, carboxymethyl starch, hydroxyethyl starch, hydroxypropyl starch).

Other useful polysaccharides include scleroglucans comprising a linear chain of (1-3) linked glucose units with a (1-6) linked glucose every three units, a commercially available example of which is Clearogel™. CS11 from Michel Mercier Products Inc.

Other emulsifiers and gelling agents useful herein include materials which are primarily derived from natural sources. Non-limiting examples of these gelling agents are gums such as acacia, agar, algin, alginic acid, ammonium alginate, amylopectin, calcium alginate, calcium carrageenan, carnitine, carrageenan, dextrin, gelatin, gellan gum, guar gum, guar hydroxypropyltrimonium chloride, hectorite, hyaluronic acid, hydrated silica, hydroxypropyl chitosan, hydroxypropyl guar, karaya gum, kelp, locust bean gum, natto gum, potassium alginate, potassium carrageenan, propylene glycol alginate, *sclerotium* gum, sodium carboxymethyl dextran, sodium carrageenan, tragacanth gum, xanthan gum, and mixtures thereof.

Non-limiting examples of water-soluble synthetic polymers include sodium polyacrylate, sodium polymethacrylate, polyacrylic acid glycerin ester, carboxyvinyl polymer, polyacrylamide, polyvinyl pyrrolidone, polyvinyl methylether, polyvinyl sulfone, maleic acid copolymer, polyethylene oxide, polydiallyl amine, polyethylene imine, water soluble cellulose derivatives (for example, carboxymethyl cellulose, methyl cellulose, methylhydroxypropyl cellulose, hydroxyethyl cellulose, hydroxypropyl cellulose, cellulose sulfate sodium salt), and starch derivatives (for example, starch oxide, dialdehyde starch, dextrin, British gum, acetyl starch, starch phosphate, carboxymethyl starch, hydroxyethyl starch, hydroxypropyl starch).

As used herein, the term "silicone oil" is an oil (or non-aqueous medium) which is capable of evaporating on contact with the skin in less than one hour at ambient temperature and atmospheric pressure. The silicon oil is a cosmetic oil which is liquid at ambient temperature, having in particular a non-zero vapour pressure, at ambient temperature and atmospheric pressure, in particular having a vapour pressure ranging from 0.13 Pa to 40 000 Pa (10-3 to 300 mm Hg), and preferably ranging from 1.3 Pa to 13 000 Pa (0.01 to 100 mm Hg), and preferentially ranging from 1.3 Pa to 1300 Pa (0.01 to 10 mm Hg).

The cleansing masks compositions described herein may be free or essentially free of perfluoro compounds.

As used herein, the term "free of perfluoro compound" means that, while it is preferable that no perfluoro is present in the composition of the invention, it is possible to have very small amounts of perfluoro in the compositions, provided that these amounts do not materially affect the advantageous properties of the composition. Most preferably, the compositions contain no perfluoro. To the extent any perfluoro is present in the compositions, it is present at an amount of less than about 2.0% by weight, typically less than about 1.5% by weight, typically less than about 1.0% by weight, typically less than about 0.5% by weight, more typically less than about 0.1% by weight, based on the total weight of the composition. To the extent present, the perfluoro in such compositions are typically contributed by components other than the perfluoro compound.

Silicones Oils

The cleansing masks compositions described herein may contain one or more silicone oils. In some embodiments, the one or more silicone oils, may be, for example an hexamethyldisiloxane. Examples of silicone oils, may be, for instance volatile linear or cyclic silicone oils, especially those with a viscosity of less than or equal to 8 centistokes (cSt) (8×10-6 m2/s, at 25° C.) and especially containing from 2 to 10 silicon atoms and in particular from 2 to 7 silicon atoms, these silicones optionally comprising alkyl or alkoxy groups containing from 1 to 10 carbon atoms. As silicone oils that may be used in the invention, mention may be made especially of dimethicones with viscosities of 5 and 6 cSt, octamethylcyclotetrasiloxane, decamethyl-cyclopenta-siloxane, cyclohexasiloxane, dodecamethylcyclohexasiloxane, heptamethylhexyltrisiloxane, hepta-methyl-octyl-trisiloxane, hexamethyldisiloxane, decamethyl-tetrasiloxane and dodecamethylpentasiloxane, and mixtures thereof.

The total amount of silicone oils may be present in an amount from about 0.1, 0.2, 0.3, 0.4, 0.5, 0.6, 0.7, 0.8, 0.95, 1, 1.1, 1.2, 1.4, 1.5, 1.6, 1.8, 2, 2.4, 2.6, 2.8, 3, 3.2, 3.4, 3.6, 3.8 to about 3.8, 4, 4.1, 4.2, 4.3, 4.4, 4.5, 4.6, 4.7, 4.8, 4.9, or 5 wt. of the total weight of the cleansing mask composition.

Water Soluble Skin Active Ingredients

Additionally, this invention has utility as a deep skin cleanser and/or to deposit water-soluble actives onto the skin as it is left on the skin for at least 5 and up to 15 minutes, whereas traditional rinse-off cleansers only contact the skin for less than 1 minute and then are rinsed away with water.

The cosmetic compositions described herein may include one or more skin active ingredients. Non-limiting examples skin active agents include adenosine, 2-[4-(2-hydroxyethyl)

piperazin-1-yl] ethanesulfonic acid (HEPES), hyaluronic acid, lanolin, citric acid, malic acid, lactic acid, tartaric acid, salicylic acid, vitamin C, a vitamin, a retinoid, retinal, retinoic acid, a carotenoid, an amino acid, a protein, an enzyme, and a coenzyme. In some cases, the skin active ingredient is adenosine.

In one embodiment, the cosmetic compositions include a skin active ingredient such as a humectant and moisturizing ingredients, an anti-aging agent, a depigmenting agent, an anti-wrinkle agent, or an agent that treats oily skin.

Humectants and moisturizing ingredients may be in particular glycerol and its derivatives, urea and its derivatives, especially Hydrovance marketed by National Starch, lactic acid, hyaluronic acid, AHA, BHA, sodium pidolate, xylitol, serine, sodium lactate, ectoin and its derivatives, chitosan and its derivatives, collagen, plankton, an extract of Imperata cylindra sold under the name Moist 24 by Sederma, homopolymers of acrylic acid as Lipidure-HM of NOF Corporation, beta-glucan and in particular sodium carboxymethyl beta-glucan Mibelle-AG-Biochemistry, a mixture of oils passionflower, apricot, corn, and rice bran sold by Nestle under the name NutraLipids, a C-glycoside derivatives, in particular the C-13-D-xylopyranoside-2-hydroxypropane in the form of a solution at 30% by weight of active material in a water/propylene glycol mixture (60/40 wt %) as the product produced by the company Chimex under the trade name "Mexoryl SBB", a rose hip oil marketed by Nestle, a micro-algae extract Prophyridium cruentum enriched with zinc, marketed under the name by Vincience Algualane Zinc spheres of collagen and chondroitin sulfate of marine origin (Atelocollagen) sold by the company Engelhard Lyon under the name Marine Filling Spheres, hyaluronic acid spheres such as those marketed by Engelhard Lyon, and arginine.

Depigmenting agents include vitamin C and its derivatives and especially vitamin CG, CP and 3-O ethyl vitamin C, alpha and beta arbutin, ferulic acid, lucinol and its derivatives, kojic acid, resorcinol and derivatives thereof, tranexamic acid and derivatives thereof, gentisic acid, homogentisic, methyl gentisate or homogentisate, dioic acid, D pantheteine calcium sulphonate, lipoic acid, ellagic acid, vitamin B3, linoleic acid and its derivatives, ceramides and their counterparts, derived from plants such as chamomile, bearberry, the aloe family (*vera, ferox, bardensis*), mulberry, skullcap, a water kiwi fruit (*Actinidia chinensis*) marketed by Gattefosse, an extract of *Paeonia suffruticosa* root, such as that sold by Ichimaru Pharcos under the name Liquid Botanpi Be an extract of brown sugar (*Saccharum officinarum*) such as molasses extract marketed by Taiyo Kagaku under the name Liquid Molasses, without this list being exhaustive. Particular depigmenting agents include vitamin C and its derivatives and especially vitamin CG, CP and 3-O ethyl vitamin C, alpha and beta arbutin, ferulic acid, kojic acid, resorcinol and derivatives, D pantheteine calcium sulfonate, lipoic acid, ellagic acid, vitamin B3, a water kiwi fruit (*Actinidia chinensis*) marketed by Gattefosse, an extract of *Paeonia suffruticosa* root, such as that sold by the company Ichimaru Pharcos under the name Botanpi Liquid B.

The term "anti-wrinkle active" refers to a natural or synthetic compound producing a biological effect, such as the increased synthesis and/or activity of certain enzymes, when brought into contact with an area of wrinkled skin, this has the effect of reducing the appearance of wrinkles and/or fine lines. Exemplary anti-wrinkle actives may be chosen from: desquamating agents, anti-glycation agents, inhibitors of NO-synthase, agents stimulating the synthesis of dermal or epidermal macromolecules and/or preventing their degradation, agents for stimulating the proliferation of fibroblasts and/or keratinocytes, or for stimulating keratinocyte differentiation reducing agents; muscle relaxants and/or dermo-decontracting agents, anti-free radical agents, and mixtures thereof.

The cleansing mask compositions may include 10 ppm to 10 wt. % (100,000 ppm), 10 ppm to 5 wt. % (50,000 ppm), 10 ppm to 2.5 wt. % (25,000 ppm), 10 ppm to 1 wt. % (10,000 ppm), 10 ppm to 0.5 wt. % (5,000 ppm), 10 ppm to 0.1 wt. % (1,000 ppm), or 10 ppm to 500 ppm of one or more skin active ingredients. In some cases, the one or more skin active ingredients is present in an amount from 10, 20, 30, 40, 50, 60, 70, 80, 90, 100, 150, or 200 ppm to 500, 600, 700, 800, 900, 0.1 wt. % (1000 ppm), 0.5 wt. % (5,000 ppm), 1 wt. % (10,000 ppm)), 5 wt. % (50,000 ppm), or 10 wt. % (100,000 ppm).

Cosmetically Acceptable Carrier

The water and or the glycols in the compositions typically form part or all of a cosmetically acceptable carrier. The cosmetically acceptable carrier can include, for example, glycerin, C1-4 alcohols, organic solvents, fatty alcohols, fatty ethers, fatty esters, polyols, glycols, vegetable oils, mineral oils, liposomes, laminar lipid materials, water, or any combinations thereof. As examples of organic solvents, non-limiting mentions can be made of monoalcohols and polyols such as ethyl alcohol, isopropyl alcohol, propyl alcohol, benzyl alcohol, and phenylethyl alcohol, or glycols or glycol ethers such as, for example, monomethyl, monoethyl and monobutyl ethers of ethylene glycol, propylene glycol or ethers thereof such as, for example, monomethyl ether of propylene glycol, butylene glycol, hexylene glycol, dipropylene glycol as well as alkyl ethers of diethylene glycol, for example monoethyl ether or monobutyl ether of diethylene glycol. Other suitable examples of organic solvents are ethylene glycol, propylene glycol, butylene glycol, hexylene glycol, propane diol, and glycerin. The organic solvents can be volatile or non-volatile compounds.

In some instances, cosmetically acceptable carriers may comprise water, a mixture of water and at least one cosmetically acceptable organic solvent, or at least one cosmetically acceptable organic solvent. Additionally, cosmetically acceptable carriers may be or may include ethanol, a glycol ether, for example, dipropylene glycol n-butyl ether, isododecane, mineral oil, propylene glycol, pentylene glycol, hexylene glycol, glycerol, and mixtures thereof.

Optional Components

In one embodiment, the composition may include optional components selected from the group consisting of actives, fragrance, preservatives, and combinations thereof. The actives are selected from the group consisting of butylated hydroxytoluene, tocopherol, tocopheropl derivatives, tocotrienol, tocotrienol derivatives, ascorbic acid, ascorbic acid derivatives, ascorbyl palmitate, vitamin E, vitamin C, and combinations thereof.

The compositions may also include any other adjuvant or additive that is usually used in the field of self-cleansing products. A person skilled in the art would know which adjuvants and/or additives to select to achieve the desired results (e.g. preservatives) without adversely affecting the properties of claimed emulsions. For example, such additives include preserving agents (e.g. phenoxyethanol, sodium benzoate, benzoic acid), consistency regulators (e.g. isopropyl alcohol), thickeners, antioxidants, fragrances, and mixtures thereof.

The above ingredients lists are only examples and not limiting.

The compositions according to the instant disclosure may be prepared according to techniques that are well known to those skilled in the art, in particular those intended for the preparation of shaving compositions.

The instant disclosure will be better understood from the examples that follow, all of which are intended for illustrative purposes only and are not meant to limit the scope of the instant disclosure in any way.

As used herein, the terms "comprising," "having," and "including" are used in their open, non-limiting sense.

The terms "a," "an," and "the" are understood to encompass the plural as well as the singular.

The expression "at least one" means one or more and thus includes individual components as well as mixtures/combinations.

The expression "one or more" as used herein includes individual components as well as mixtures/combinations.

Other than in the operating examples, or where otherwise indicated, all numbers expressing quantities of ingredients and/or reaction conditions are to be understood as being modified in all instances by the term "about," meaning within +/−5% of the indicated number.

All ranges and values disclosed herein are inclusive and combinable. For examples, any value or point described herein that falls within a range described herein can serve as a minimum or maximum value to derive a sub-range, etc.

All percentages, parts and ratios herein are based upon the total weight of the compositions of the present disclosure, unless otherwise indicated.

All ranges and values disclosed herein are inclusive and combinable. For examples, any value or point described herein that falls within a range described herein can serve as a minimum or maximum value to derive a sub-range, etc.

Furthermore, all ranges provided are meant to include every specific range within, and combination of sub-ranges between, the given ranges. Thus, a range from 1-5, includes specifically 1, 2, 3, 4 and 5, as well as sub ranges such as 2-5, 3-5, 2-3, 2-4, 1-4, etc.

All publications and patent applications cited in this specification are herein incorporated by reference, and for any and all purposes, as if each individual publication or patent application were specifically and individually indicated to be incorporated by reference. In the event of an inconsistency between the present disclosure and any publications or patent application incorporated herein by reference, the present disclosure controls.

While the disclosure has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

Example 1

Cleansing Composition

The following Examples are provided for illustrative purposes only, and are not intended to be limiting.

TABLE 1

| Claims | INCI name | Inventive Example Inventive ex. 1 |
|---|---|---|
| a | POLYVINYL ALCOHOL | 12.5 |
| b | HYDROGENATED STARCH HYDROLYSATE | 0.7 |
| c | DISODIUM LAURETH SULFOSUCCINATE | 0.9 |
|   | SODIUM LAURYL SULFOACETATE | 0.35 |
| c | PEG-7 GLYCERYL COCOATE | 0.5 |
| c | COCO-BETAINE | 1.25 |
| d | CETYL HYDROXYETHYLCELLULOSE | 0.5 |
| e | DISILOXANE | 2.00 |
|   | PRESERVATIVE | 0.6 |
|   | GLYCERIN; PEG-90 | 3.00 |
|   | WATER/AQUA | Q.S. |

In making the formulation in the above table, the following procedure was used. Solvents and preservatives were mixed together at 20-25° C. Polyvinyl alcohol was added to the kettle under maximum agitation. 20 grams of cold water per 100 grams formula was added. The solution was heated to 80° C., maintaining maximum agitation possible without foam formation, and allowed to mix until gel bodies were no longer visible. The cetyl hydroxyethylcellulose was dispersed in glycerin and then added to the kettle. The solution was cooled to 25-30° C. with stirring. The surfactants were mixed in 10 grams of water per 100 grams formula and then added to the kettle. Disiloxane was added to the kettle and homogenized for 15 minutes.

Example 2

Inventive and Comparative Examples

The following Examples are provided for illustrative purposes only, and are not intended to be limiting.

The inventive and comparative Examples were studied. The bubble formation, the film integrity, the film peelability, and the suspension of the silicone were assessed visually. Dry time of the formulas were also measured. The objectives were to invent a product that:

1) self-bubbled
2) dried into a film in less than 10 minutes, and
3) formed a film that can be peeled away from the skin in 1 piece with little to no residual product left on the skin.

The peel-off mask is applied as a film that is thinly spread with fingers on the face. It is allowed to dry for several minutes, then peeled away from face with fingers. It peels-off in one piece as a film. It is usually preferred that such masks require a relatively short period of time to dry down to be peeled away. Such peel-off masks usually provide deep pore cleansing, skin debris removal functions.

TABLE 2

Inventive and Comparative Examples

| | Inv. Ex. 1 | Comp. Ex. 1 | Comp. Ex. 2 | Comp. Ex. 3 | Comp. Ex. 4 | Comp. Ex. 5 |
|---|---|---|---|---|---|---|
| Attributes | | Known Self-bubbling cleanser | Attempt to add the peel-away agent (polyvinyl alcohol) to Comp. Ex. 1 | Peel-away mask formula | addition of the self-bubbling agent (disiloxane) to Comp. Ex. 3 | Mix of aspects of (Comp. Ex. 1) Self-bubbling cleanser and (Comp. Ex. 3) |
| Objectives | | | | | | |
| Self-bubbles | + | + | + | − | − | + |
| Dries into film | + | − | + | + | + | + |
| Film dries within 10 minutes | + | − | − | + | + | + |
| Can be peeled away from the skin | + | − | − | + | + | + |
| Can easily be peeled in one piece | + | − | − | + | + | + |
| Leaves no residual product on the skin | + | − | − | + | + | + |
| Cleanses | + | + | + | − | − | + |
| Stable (no visual separation) | + | + | − | + | − | − |
| Key raw materials | | | | | | |
| POLYVINYL ALCOHOL | 12.5 | 0 | 6 | 9.5 | 9.5 | 9.5 |
| HYDROGENATED STARCH HYDROLYSATE | 0.7 | 0 | 0 | 0.7 | 0.7 | 0.7 |
| DISODIUM LAURETH SULFOSUCCINATE | 0.9 | 2.16 | 2.16 | 0 | 0 | 0.45 |
| SODIUM LAURYL SULFOACETATE | 0.35 | 0.84 | 0.84 | 0 | 0 | 0.17 |
| PEG-7 GLYCERYL COCOATE | 0.5 | 1 | 1 | 0 | 0 | 0 |
| COCO-BETAINE | 1.25 | 4.2 | 4.2 | 0 | 0 | 0.75 |
| CETYL HYDROXYETHYLCELLULOSE (CHEC) | 0.5 | 0 | 0 | 0 | 0 | 0 |
| Hydroethylcellulose | 0 | 0.15 | 0.15 | 0 | 0 | 0 |
| DISILOXANE | 2 | 2 | 2 | 0 | 2 | 2 |
| Key learning | Inv. Formula | No peelable film was observed | Simply adding PVA to self-bubbling cleanser does not result in peelable film | A peelable film is formed, but no self-bubbling and no cleansing properties are observed | Simply adding disiloxane to peel-away mask does not result in a self-bubbling formula | Mixing relevant ingredients of both formulas does not result in stable formula |

| | Comp. Ex. 6 | Comp. Ex. 7 | Comp. Ex. 8 | Comp. Ex. 9 | Comp. Ex. 10 | Comp. Ex. 11 |
|---|---|---|---|---|---|---|
| Rationale | Substitution of xanthan gum for CHEC | Inv ex. 1 minus CHEC | Inv ex. 1 minus disiloxane | Inv ex. 1 minus PVA | Inv. Ex. 1 minus starch | Inv ex. 1 minus surfactants |
| Objectives | | | | | | |
| Self-bubbles | + | + | − | − | + | − |
| Dries into film | + | + | + | − | + | + |
| Film dries within 10 minutes | + | + | + | − | + | + |
| Can be peeled away from the skin | + | + | + | − | − | + |
| Can easily be peeled in one piece | + | − | + | − | − | − |
| Leaves no residual product on the skin | + | − | + | − | − | − |
| Cleanses | + | + | + | + | + | − |
| Stable (no visual separation) | − | − | + | − | + | + |

TABLE 2-continued

Inventive and Comparative Examples

| Key raw materials | | | | | | |
|---|---|---|---|---|---|---|
| POLYVINYL ALCOHOL | 12.5 | 12.5 | 12.5 | 0 | 12.5 | 12.5 |
| HYDROGENATED STARCH HYDROLYSATE | 0.7 | 0.7 | 0.7 | 0.7 | 0 | 0.7 |
| DISODIUM LAURETH SULFOSUCCINATE | 0.9 | 0.9 | 0.9 | 0.9 | 0.9 | 0 |
| SODIUM LAURYL SULFOACETATE | 0.35 | 0.35 | 0.35 | 0.35 | 0.35 | 0 |
| PEG-7 GLYCERYL COCOATE | 0.5 | 0.5 | 0.5 | 0.5 | 0.5 | 0 |
| COCO-BETAINE | 1.25 | 1.25 | 1.25 | 1.25 | 1.25 | 0 |
| CETYL HYDROXYETHYLCELLULOSE (CHEC) | 0 | 0 | 0.5 | 0.5 | 0.5 | 0.5 |
| Hydroxyethylcellulose | 0 | 0 | 0 | 0 | 0 | 0 |
| XANTHAM GUM | 0.5 | 0 | 0 | 0 | 0 | 0 |
| DISILOXANE | 2 | 2 | 0 | 2 | 2 | 2 |
| Key learning | Thickener must be hydrophobically-modified to successfully stabilize silicone; choice of thickener matters | Without the thickener, the invention phase separates and loses peel-ability | The formula can be stabilized if the silicone is removed, but then there is no self-bubbling action; similar to the peel-away mask (comp. ex. 3), but with added cleansing function | Without PVA, the formula becomes an unstable cleanser with no peel-away function and no bubbling action | The starch enhances film formation and peel-ability of the formula | Without the surfactants, there is no cleansing and no bubbling action, indicating that the surfactant micelles help to stabilize the silicone |

Comp. Ex. 1

Comp. Ex. 1 was a cleansing formula that was known to self-bubble, but didn't have a peel-away ability. It didn't contain polyvinyl alcohol.

Comp. Ex. 2

Comp. Ex. 2 contained polyvinyl alcohol. It was observed that the addition of that ingredient to the self-bubbling cleanser (i.e. Comp. Ex. 1) extended the bubbles' lifetime, but did not lead to a product that dried down into a peelable film.

Comp. Ex. 3

Comp. Ex. 3 was a formula that dried down into a peelable film but did not cleanse or form any bubbles. The material that provided the self-bubbling action to Comp. Ex. 1, disiloxane, was added to the formula (i.e. Comp. Ex. 4). It was then observed that even though the material that provided the self-bubbling action to Comp. Ex. 1 was added the formula, it did not form any bubbles. So the addition of the material that provided the self-bubbling action to Comp. Ex. 1 to a peel-away mask formula was not enough to create a formula that both peels away from the skin and is self-bubbling.

Comp. Ex. 5

Comp. Ex. 5 included relevant key materials from the self-bubbling formula (i.e. Comp. Ex. 1) and the peel-away mask (i.e. Comp. Ex. 3). It was prepared with solvents, preservatives, polyvinyl alcohol, the agent used to induce self-bubbling disiloxane, and the surfactants which provide the cleansing action. A secondary film former, hydrogenated starch hydrolysate, was also added to enhance film formation and peel-away ability. The result was a gel that met all three objectives of the invention; however, the gel phase separated within 24 hours.

Comp. Ex. 6

Comp. Ex. 6 was comparable to Comp. Ex. 5, but glycerin and a polymeric thickener, xanthan gum, were added to the mixture. This resulted in a thickened gel that also met all three objectives of the invention and phase separated within 24 hours. An alternative polymeric thickener, cetyl hydroxyethylcellulose (CHEC), was substituted for xanthan gum and the result was a stabilized formula that met all three objectives of the invention, i.e. Inv. Ex. 1. Thus, the choice of polymeric thickener impacted the stability of the invention. Specifically, a hydrophobically-modified polymer was required to stabilize the silicone in the aqueous formula.

Comp. Ex. 7

Comp. Ex. 7 was comparable to Comp. Ex. 6, but there was no cetyl hydroxyethylcellulose (CHEC). It was observed that without the thickener, the invention phase separated and lost peel-ability Comp. Ex. 8

When the disiloxane was removed from Inv. Ex. 1, the formula was comparable to a peel-away mask (i.e. Comp. Ex. 3) with added cleansing ability. It did not self-bubble. Thus, a silicone that was pseudo-stable in the formula but rapidly evaporated when the formula was spread thin was required for the self-bubbling action.

Comp. Ex. 9

When the film former, polyvinyl alcohol was removed from Inv. Ex. 1, the formula became an unstable cleanser with no peel away action and no self-bubbling action. With only polyvinyl alcohol or hydrogenated starch hydrolysate in Inv. Ex. 1, the formula self-bubbled and dried down into a film, but the film was not easily peeled away from the skin and left residue. Thus, both film formers were required to achieve a substantial film that could be peeled away from the skin.

Comp. Ex. 10

When the film former was removed from Inv. Ex. 1, the formula did not self-bubble or cleansed well. It did dry down into a film that could be peeled away from the skin, but was not easily removed and left behind residual product. Thus, surfactants were required for cleansing and bubbling action. Furthermore, the surfactant concentration must be above the critical micelle concentration of the surfactant blend to achieve these actions. The starch enhanced film formation and peel-ability of the formula.

Comp. Ex. 11

Comp. Ex. 11 didn't contain any of the surfactants that were present in Inventive. Ex. 1. Without the surfactants, there was no cleansing and no bubbling action, indicating that the surfactant micelles helped to stabilize the silicone While the disclosure has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A cleansing mask composition comprising:
    a) from about 8 to about 20 wt. % of a polyvinyl alcohol;
    b) from about 0.2 to about 10 wt. % of at least one sugar alcohol;
    c) from about 0.1 to about 50 wt. % of at least one surfactant;
    d) from about 0.2 to about 2 wt. % of at least one or more hydrophobically-modified polymers;
    e) from about 0.1 to 5 wt. % of at least one silicone oil;
    f) water; and
    wherein the composition provides a self-bubbling action;
    wherein the cleansing mask composition is free of perfluoro compounds; and
    wherein the weight percentages are based on the total weight of the cleansing composition.

2. The composition of claim 1 that peels away in one piece from the skin.

3. The composition of claim 1, wherein the self-bubbling starts immediately after application of the composition onto the skin.

4. The composition of claim 1, wherein the at least one sugar alcohols is selected from the group consisting of isomalt, mannitol, galactilol, fucitol, iditol, volemitol, lactilol, maltotriiol, maltotetraitol, polyglycitol, sorbitol, xylitol, lactitol, maltitol, inositol, erythritol, hydrogenated starch hydrolysates, and mixtures thereof.

5. The composition of claim 1, wherein the at least one surfactant is selected from the group consisting of anionic surfactants, non-ionic surfactants, zwitterionic surfactants and combinations thereof.

6. The composition of claim 1, wherein the at least one surfactant is selected from disodium laureth sulfosuccinate, sodium lauryl sulfoacetate, PEG-7 glyceryl cocoate, cocobetaine and combinations thereof.

7. The composition of claim 1, wherein the one or more hydrophobically-modified polymers is selected from cetyl hydroxyethylcellulose, acrylates/beheneth-25 methacrylate copolymer, acrylates/c10-30 alkyl acrylate crosspolymer, acrylates/vinyl neodecanoate crosspolymer, ammonium acryloyldimethyltaurate/steareth-25 methacrylate crosspolymer, ammonium polyacryloyldimethyl taurate, glyceryl polyacrylate, ethyl hydroxyethylcellulose, methyl hydroxyethylcellulose, hydroxypropyl guar, hydroxypropyl starch phosphate, peg-240/hdi copolymer bis-decyltetradeceth-20 ether, polyacrylate crosspolymer-6, steareth-100/peg-136/hdi copolymer, and combination thereof.

8. The composition of claim 1, wherein the at least one silicone oil is a cyclic or linear silicone molecule having a viscosity of less than 8 cst.

9. The composition of claim 1, wherein the at least one silicone oil is selected from disiloxane, hexamethyldisiloxane, divinyltetramethyldisiloxane, octamethyldisiloxane, decamethyltetrasiloxane, dodecamethylpentasiloxane, hexadecamethylheptasiloxane, hexamethylcyclotrisiloxane, tetradecamethylhexasiloxane, octamethylcyclotetrasiloxane, decamethylcyclopentasiloxane, dodecamethylcyclohexasiloxane, polydimethylsiloxane, ethyl trisiloxane, and combinations thereof.

10. The composition of claim 9, wherein the at least one silicone oil is present from about 0.2 to 5 wt. % of the total weight of the cleansing composition.

11. The composition of claim 1, wherein the self-bubbling action is provided by the presence of the at least one silicone oil.

12. A cleansing mask composition comprising:
    a) from about 6 to about 20 wt. % of polyvinyl alcohol;
    b) from about 0.2 to about 10 wt. % of at least one sugar alcohol comprising Hydrogenated Starch hydrolysate;
    c) from about 0.1 to about 50 wt. % of at least one surfactant selected from disodium laureth sulfosuccinate, sodium lauryl sulfoacetate, PEG-7 glyceryl cocoate, coco-betaine and combination thereof;
    d) from about 0.2 to about 2 wt. % of at least one hydrophobically-modified polymer comprising cetyl hydroxyethylcellulose;
    e) from about 0.2 to about 5 wt. % of disiloxane;
    f) water; and
    wherein the composition provides the self-bubbling action;
    wherein the cleansing mask composition is free of perfluoro compounds; and
    wherein the weight percentages are based on the total weight of the cleansing composition.

13. A method for cleansing the skin comprising applying the composition of claim 1 to the skin and removing the composition from the skin by peeling away the composition in one piece.

14. A method for cleansing the face comprising applying the cleansing composition of claim 1 to the face and cleansing the face.

* * * * *